(12) United States Patent
Burbar et al.

(10) Patent No.: US 11,974,866 B2
(45) Date of Patent: May 7, 2024

(54) MODEL-BASED INJECTED DOSE OPTIMIZATION FOR LONG AXIAL FOV PET IMAGING

(71) Applicant: Siemens Medical Solutions USA, Inc., Malvern, PA (US)

(72) Inventors: Ziad Burbar, Knoxville, TN (US); Inki Hong, Knoxville, TN (US); Stefan B. Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 245 days.

(21) Appl. No.: 17/596,837

(22) PCT Filed: Oct. 1, 2019

(86) PCT No.: PCT/US2019/053982
§ 371 (c)(1),
(2) Date: Dec. 20, 2021

(87) PCT Pub. No.: WO2021/066808
PCT Pub. Date: Apr. 8, 2021

(65) Prior Publication Data
US 2022/0296180 A1 Sep. 22, 2022

(51) Int. Cl.
*A61B 6/03* (2006.01)
*A61B 6/00* (2006.01)
*A61B 6/04* (2006.01)

(52) U.S. Cl.
CPC ............ *A61B 6/037* (2013.01); *A61B 6/0407* (2013.01); *A61B 6/5294* (2013.01)

(58) Field of Classification Search
CPC ......... A61B 6/037; A61B 6/08; A61B 6/4057; A61B 6/42; A61B 6/4208; A61B 6/4266; A61B 6/4275; A61B 6/544; A61B 6/547; A61B 2576/02
See application file for complete search history.

(56) References Cited

U.S. PATENT DOCUMENTS

| | | |
|---|---|---|
| 7,180,074 B1 | 2/2007 | Crosetto |
| 2004/0206897 A1 | 10/2004 | Conti et al. |
| 2009/0127468 A1* | 5/2009 | Fehrenbacher ........... G01T 1/06 250/370.07 |
| 2014/0193336 A1* | 7/2014 | Rousso ................. A61B 6/503 600/431 |
| 2017/0146672 A1* | 5/2017 | Chen ................... G01T 1/20182 |

(Continued)

FOREIGN PATENT DOCUMENTS

WO 2018115039 6/2018

OTHER PUBLICATIONS

International Search Report for Corresponding PCT Application No. PCT/US2019/053982 dated Jun. 3, 2020.

(Continued)

*Primary Examiner* — Gerald Johnson (57) ABSTRACT

A computer-implemented method for determining scan parameters includes receiving a set of input parameters. An average single per block for a nuclear imaging scanner having a predetermined field-of-view (FOV) is determined based on the input parameters and at least one scan parameter is determined based on the average single per block for the nuclear imaging scanner.

20 Claims, 6 Drawing Sheets

(56) References Cited

U.S. PATENT DOCUMENTS

2018/0203141 A1 7/2018 Chang et al.
2019/0320989 A1* 10/2019 Verma .................... A61B 6/037

OTHER PUBLICATIONS

Jonathan K Poon et al: "A simulation study of a long axial field of view whole-body PET scanner using cylindrical and anthropomorphic phantoms", Nuclear Science Symposium Conference Record, 2008. NSS 108. IEEE (Oct. 19-25, 2008), IEEE, Piscataway, NJ, USA, Oct. 19, 2008 (Oct. 10, 2008), pp. 4999-5006.

* cited by examiner

MODEL-BASED INJECTED DOSE OPTIMIZATION FOR LONG AXIAL FOV PET IMAGING

TECHNICAL FIELD

This application relates generally to nuclear imaging and, more particularly, to long axial field-of-view nuclear imaging.

BACKGROUND

Current short axial field-of-view (FOV) scanner axial extents vary by less than about 10 cm and have imaging diameters of about 80 cm. For short axial FOV scanners, the same distribution of a singles rate at a detector for a given organ and radiotracer may be assumed without regard to geometrical differences. When using radiotracer compounds with a short half-life, e.g., O-15, Rb-82, etc., a patient may be injected with a very high dose so that the short axial FOV system is able to collect a sufficient quantity of data (e.g., statistics) to generate reconstructions. For long axial FOV systems, sensitivity and the data throughput are increased.

The radiotracer compounds target specific organs that are subsequently imaged. Because of this targeting (i.e., concentration) the singles count rates at a detector level are not distributed in the same manner as in a long axial FOV system. The long axial FOV system has an increased detection count and distribution due to additional organs in the body that may not have the same uptake (i.e., concentration) of radiotracer as the targeted organ.

SUMMARY

In some embodiments a computer-implemented method is disclosed. The computer-implemented method includes a step of receiving a set of input parameters. An average single per block for a nuclear imaging scanner having a predetermined field-of-view (FOV) is determined based on the input parameters and at least one scan parameter is determined based on the average single per block for the nuclear imaging scanner In some embodiments a system is disclosed. The system includes a nuclear imaging scanner and a computer. The computer is configured to receive a set of input parameters, determine an average single per block for a field-of-view (FOV) of the nuclear imaging scanner based on the input parameters, and determine at least one scan parameter based on the average single per block for the nuclear imaging scanner.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

The description of the preferred embodiments is intended to be read in connection with the accompanying drawings, which are to be considered part of the entire written description of this invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise. The term "operatively coupled" is such an attachment, coupling, or connection that allows the pertinent structures to operate as intended by virtue of that relationship. In the claims, means-plus-function clauses, if used, are intended to cover structures described, suggested, or rendered obvious by the written description or drawings for performing the recited function, including not only structure equivalents but also equivalent structures.

Figure 1:
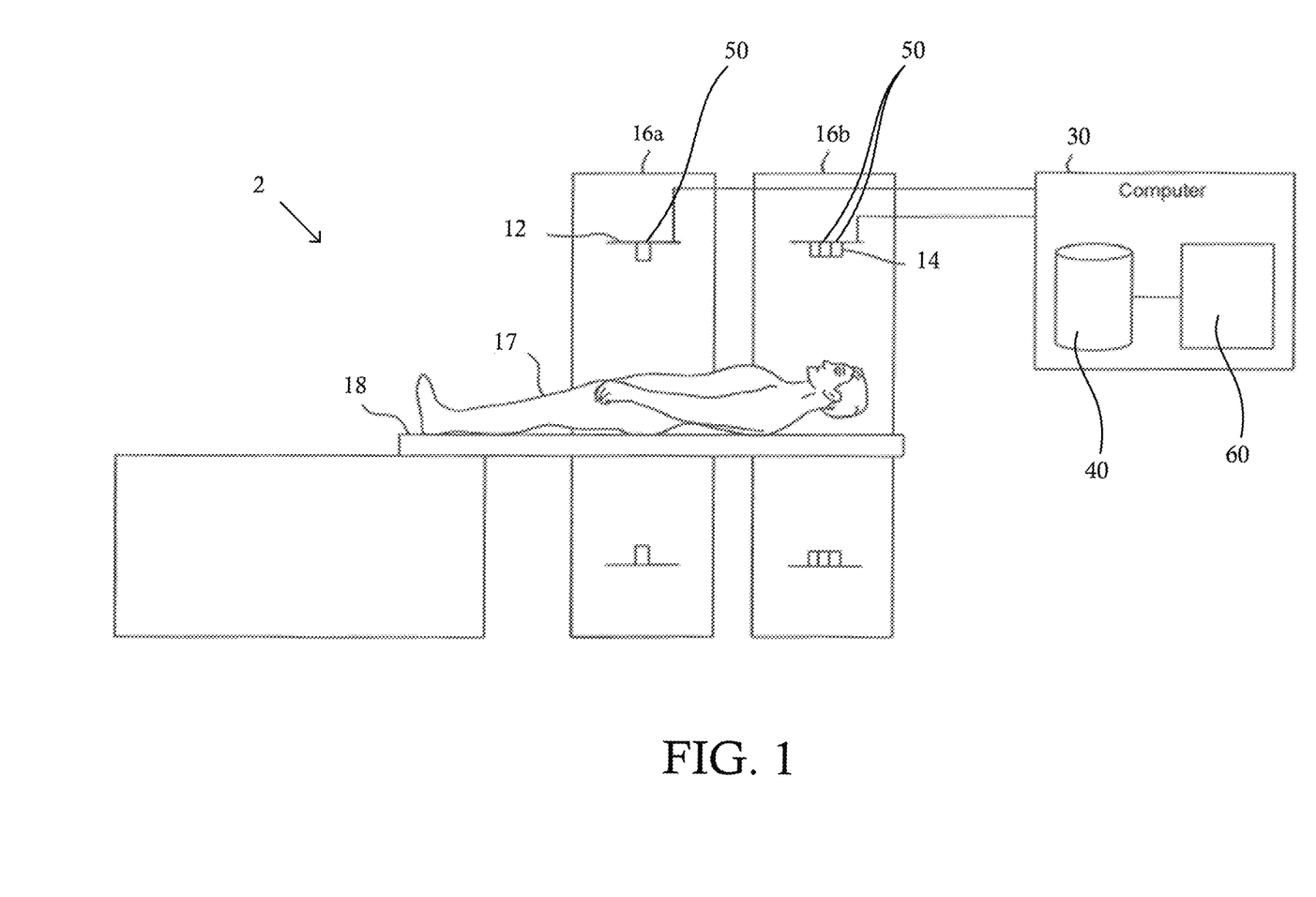
FIG. 1 illustrates a nuclear imaging system, in accordance with some embodiments.

FIG. 1 illustrates one embodiment of a nuclear imaging system 2. The nuclear imaging system 2 includes a scanner for at least a first modality 12 provided in a first gantry 16a. The first modality 12 may include any suitable modality, such as, for example, a computed-tomography (CT) modality, a positron-emission tomography (PET) modality, a single-photon emission computerized tomography (SPECT) modality, etc. The first modality 12 may include a long axial FOV scanner or a short axial FOV scanner. A patient 17 lies on a movable patient bed 18 that may be movable with respect to the first gantry 16a. In some embodiments, the nuclear imaging system 2 includes a scanner for a second modality 14 provided in a second gantry 16b. The second modality 14 can be any suitable imaging modality, such as, for example, a CT modality, a PET modality, a SPECT modality and/or any other suitable imaging modality. The second modality 14 may include a long axial FOV scanner or a short axial FOV scanner. Each of the first modality 12 and/or the second modality 14 can include one or more detectors 50 configured to detect an annihilation photon, gamma ray, and/or other nuclear imaging event.

Scan data from the first modality 12 and/or the second modality 14 is stored at one or more computer databases 40 and processed by one or more computer processors 60 of a computer system 30. The graphical depiction of computer system 30 in FIG. 1 is provided by way of illustration only, and computer system 30 may include one or more separate computing devices, for example, as described with respect to FIG. 2. The scan data may be provided by the first modality 12, the second modality 14, and/or may be provided as a separate data set, such as, for example, from a memory coupled to the computer system 30. The computer system 30 can include one or more processing electronics for processing a signal received from one of the plurality of detectors 50.

Figure 2:
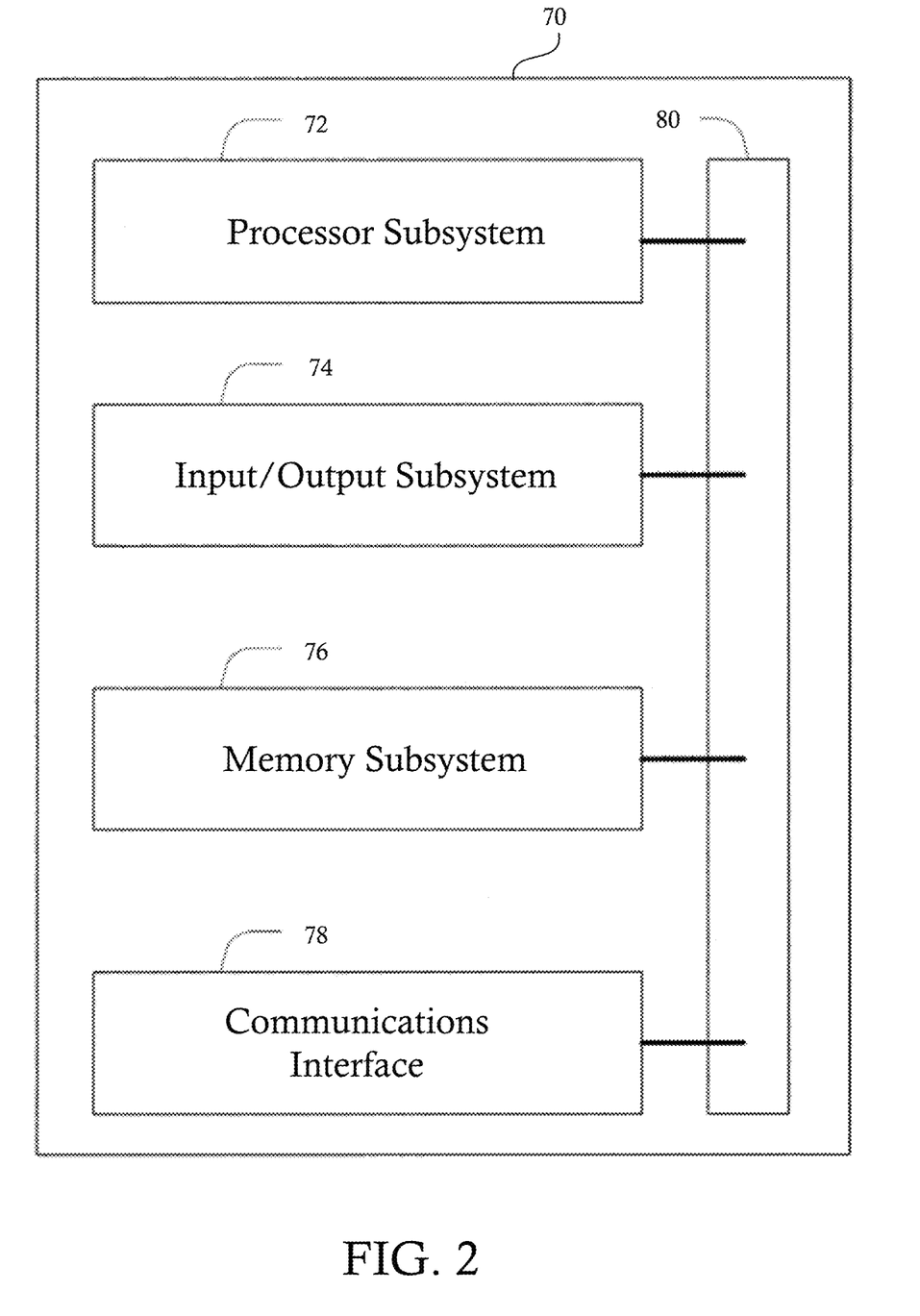
FIG. 2 illustrates a block diagram of a computer system, in accordance with some embodiments.

FIG. 2 illustrates a computer system 30 configured to implement one or more processes, in accordance with some embodiments. The system 30 is a representative device and may comprise a processor subsystem 62, an input/output subsystem 64, a memory subsystem 66, a communications interface 68, and a system bus 70. In some embodiments, one or more than one of the system 30 components may be combined or omitted such as, for example, not including an input/output subsystem 64. In some embodiments, the system 30 may comprise other components not shown in FIG. 2. For example, the system 30 may also include, for example, a power subsystem. In other embodiments, the system 30 may include several instances of a component shown in FIG. 2. For example, the system 30 may include multiple memory subsystems 66. For the sake of conciseness and clarity, and not limitation, one of each component is shown in FIG. 2.

The processor subsystem 62 may include any processing circuitry operative to control the operations and performance of the system 30. In various aspects, the processor subsystem 62 may be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 62 also may be implemented by a controller, a microcontroller, an application specific integrated circuit (ASIC), a field programmable gate array (FPGA), a programmable logic device (PLD), and so forth.

In various aspects, the processor subsystem 62 may be arranged to run an operating system (OS) and various applications. Examples of an OS comprise, for example, operating systems generally known under the trade name of Apple OS, Microsoft Windows OS, Android OS, Linux OS, and any other proprietary or open source OS. Examples of applications comprise, for example, network applications, local applications, data input/output applications, user interaction applications, etc.

In some embodiments, the system 30 may comprise a system bus 70 that couples various system components including the processing subsystem 62, the input/output subsystem 64, and the memory subsystem 66. The system bus 70 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCMCIA), Small Computers Interface (SCSI) or other proprietary bus, or any custom bus suitable for computing device applications.

In some embodiments, the input/output subsystem 6 may include any suitable mechanism or component to enable a user to provide input to system 2 and the system 2 to provide output to the user. For example, the input/output subsystem 6 may include any suitable input mechanism, including but not limited to, a button, keypad, keyboard, click wheel, touch screen, motion sensor, microphone, camera, etc.

In some embodiments, the input/output subsystem 64 may include a visual peripheral output device for providing a display visible to the user. For example, the visual peripheral output device may include a screen such as, for example, a Liquid Crystal Display (LCD) screen. As another example, the visual peripheral output device may include a movable display or projecting system for providing a display of content on a surface remote from the system 30. In some embodiments, the visual peripheral output device can include a coder/decoder, also known as Codecs, to convert digital media data into analog signals. For example, the visual peripheral output device may include video Codecs, audio Codecs, or any other suitable type of Codec.

The visual peripheral output device may include display drivers, circuitry for driving display drivers, or both. The visual peripheral output device may be operative to display content under the direction of the processor subsystem 62. For example, the visual peripheral output device may be able to play media playback information, application screens for application implemented on the system 30, information regarding ongoing communications operations, information regarding incoming communications requests, or device operation screens, to name only a few.

In some embodiments, the communications interface 68 may include any suitable hardware, software, or combination of hardware and software that is capable of coupling the system 30 to one or more networks and/or additional devices. The communications interface 68 may be arranged to operate with any suitable technique for controlling information signals using a desired set of communications protocols, services or operating procedures. The communications interface 68 may comprise the appropriate physical connectors to connect with a corresponding communications medium, whether wired or wireless.

Vehicles of communication comprise a network. In various aspects, the network may comprise local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules may communicate in accordance with a number of wired protocols. Examples of wired protocols may comprise Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 68 may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 68 may comprise a wireless interface comprising one or more antennas, transmitters, receivers, transceivers, amplifiers, filters, control logic, and so forth.

In various aspects, the communications interface 68 may provide data communications functionality in accordance with a number of protocols. Examples of protocols may comprise various wireless local area network (WLAN) protocols, including the Institute of Electrical and Electronics Engineers (IEEE) 802.xx series of protocols, such as IEEE 802.11a/b/g/n/ac, IEEE 802.16, IEEE 802.20, and so forth. Other examples of wireless protocols may comprise various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may comprise wireless personal area network (PAN) protocols, such as an Infrared protocol, a protocol from the Bluetooth Special Interest Group (SIG) series of protocols (e.g., Bluetooth Specification versions 5.0, 6, 7, legacy Bluetooth protocols, etc.) as well as one or more Bluetooth Profiles, and so forth. Yet another example of wireless protocols may comprise near-field communication techniques and protocols, such as electro-magnetic induction (EMI) techniques. An example of EMI techniques may comprise passive or active radio-frequency identification (RFID) protocols and devices. Other suitable protocols may comprise Ultra Wide Band (UWB), Digital Office (DO), Digital Home, Trusted Platform Module (TPM), ZigBee, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in memory subsystem 66.

In some embodiments, the memory subsystem 66 may comprise any machine-readable or computer-readable media capable of storing data, including both volatile/non-volatile memory and removable/non-removable memory. The memory subsystem 8 may comprise at least one non-volatile memory unit. The non-volatile memory unit is capable of storing one or more software programs. The software programs may contain, for example, applications, user data, device data, and/or configuration data, or combinations therefore, to name only a few. The software programs may contain instructions executable by the various components of the system 30.

In various aspects, the memory subsystem 66 may comprise any machine-readable or computer-readable media capable of storing data, including both volatile/non-volatile memory and removable/non-removable memory. For example, memory may comprise read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory subsystem 66 may contain an instruction set, in the form of a file for executing various methods, such as methods including A/B testing and cache optimization, as described herein. The instruction set may be stored in any acceptable form of machine readable instructions, including source code or various appropriate programming languages. Some examples of programming languages that may be used to store the instruction set comprise, but are not limited to: Java, C, C++, C#, Python, Objective-C, Visual Basic, or .NET programming. In some embodiments a compiler or interpreter is comprised to convert the instruction set into machine executable code for execution by the processing subsystem 62.

Figure 3:
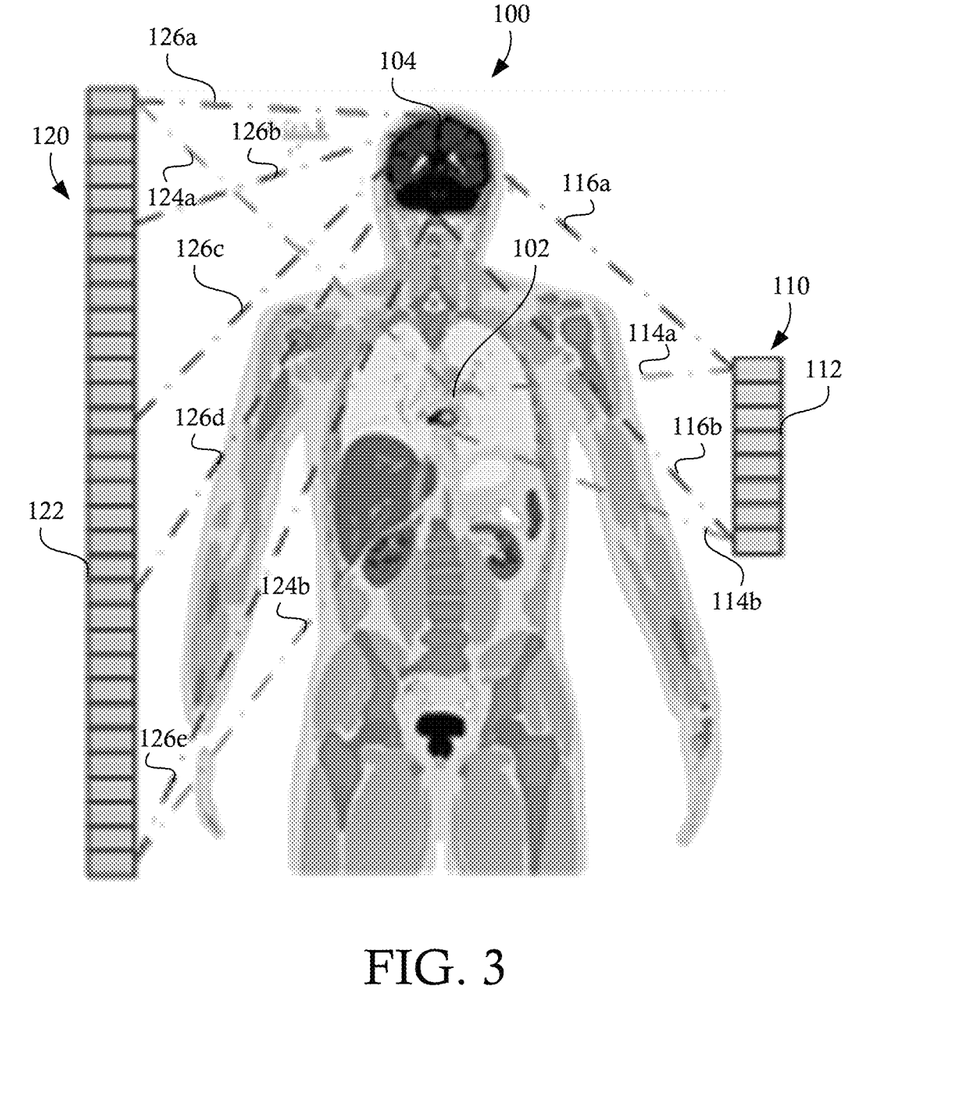
FIG. 3 illustrates organ activity distribution for a brain and a heart with respect to a long-axial FOV system and a short axial FOV system, in accordance with some embodiments.

FIG. 3 illustrates organ activity distribution for a first organ 102 and a second organ 104 with respect to a short axial FOV system 110 and a long-axial FOV system 120, in accordance with some embodiments. During scanning, a patient 100 is positioned on a bed, such as, for example, bed 18 illustrated in FIG. 1. In a short axial FOV system 110, the FOV of the detectors 112 detect a first set events 114*a*, 114*b* originating from within a first organ 102, such as the heart and a second set of events 116*a*, 116*b* originating from within a second organ 104, such as a brain. The short FOV limits the number of events detected from either the first organ 102 or the second organ 104, requiring a large dose of radiotracer (e.g., radioactive isotope) to generate adequate data for reconstruction generation. In contrast, the large axial FOV scanner 120 includes a detector 122 extending over a larger portion of a patient 100, for example, from the head to the mid-thighs. The large axial detector 122 FOV detects a first set of events 124*a*, 124*b* occurring in the first organ 102 and a second set of events 126*a*-126*e* occurring in the second organ 104. The number of events detected by the large axial FOV scanner 120 is greater than the number of events detected by the short axial FOV scanner 110.

In some embodiments, data obtained using a first axial FOV system, such as the short axial FOV system 110, may be used to estimate an expected performance of a second axial FOV system, such as the long axial FOV system 120.

Figure 4:
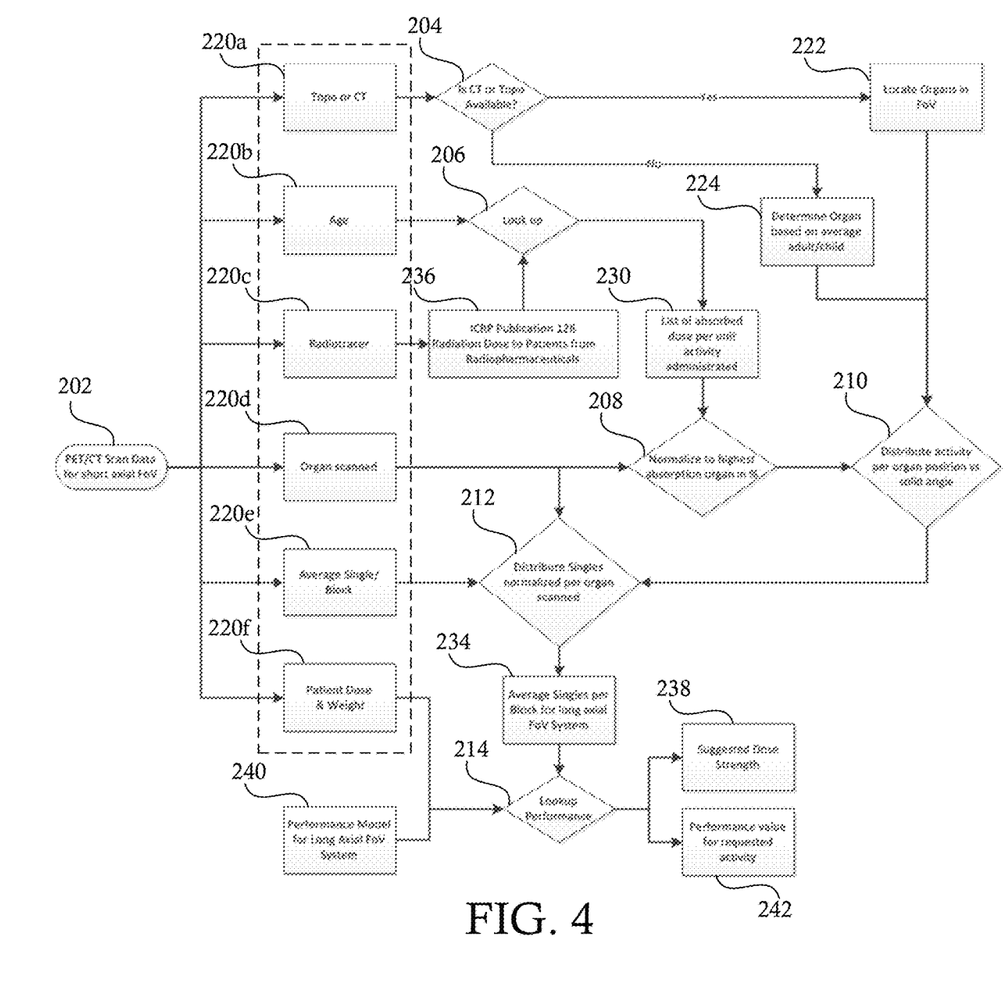
FIG. 4 is a flowchart illustrating a method of using patient data acquired on a short axial FOV system to estimate an expected performance for a long axial FOV system, in accordance with some embodiments.

FIG. 4 is a flowchart illustrating a method 200 of using patient data acquired using a short axial FOV system 110 to estimate an expected performance for a long axial FOV system 120, in accordance with some embodiments. Although embodiments are discussed herein using data from a short axial FOV system 110 to estimate performance for a long axial FOV system 120, it will be appreciated that a system having a first axial FOV (e.g., short, long, etc.) may be used to estimate any other system having a second axial FOV (e.g., short, long, etc.). At step 202, scan data 220 for one or more modalities is obtained using the short axial FOV system 110. The scan data 220 may be obtained using one or more suitable modalities, such as, for example, a CT modality, a PET modality, a SPECT modality, and/or any other suitable modality. In the illustrated embodiment, the data set includes PET and CT data.

At step 204, a system, such as computer system 30, determines whether CT or topographic scan data 220a is available. If CT or topographic scan data 220a is available (e.g., a CT scan was performed), the system locates 222 each of the organs within the FOV of the small axial FOV system 110 based on the CT scan data 220a. For example, for the embodiment illustrated in FIG. 3, the system may identify a heart 102 as being located within the FOV of the small axial FOV system 110. The system may use any suitable method to identify organ position, such as, for example, organ segmentation, a trained classification network, etc. If no CT or topographic scan data 220a is available, the system estimates 224 the position of a specific organ within the FOV using an average position for similar patients, e.g., average position for adult male, adult female, adolescent male, adolescent female, etc.

At step 206, an absorbed dose per unit activity administered 230 is determined by the system. The absorbed dose may be determined based on patient biometrics, such as the age 220b of a patient, and/or a radiotracer 220c used during the short axial FOV scan. For example, in some embodiments, a look-up table based on age 220b and the radiotracer 220c is used to determine an absorbed dose per unity activity administered 230. The look-up table may include publicly available data 236, such as, for example, data available in the ICRP Publication 128 "Radiation Dose to Patients from Radiopharmaceuticals: A Compendium of Current Information Related to Frequently Used Substances," and/or may include non-public data, such as proprietary look-up tables.

At step 208, the absorbed dose 230 is normalized for all each scanned organ 220d contained within the scan data 220. The absorbed dose 230 may be normalized by selecting an organ within the organ set 220d having the highest absorption percentage. In other embodiments, the absorbed dose 230 may be normalized using a predetermined normalization factor. At step 210, the detected activity (e.g., events) contained within the scan data 220 are distributed per organ 220d position based on a predetermined, or solid, angle. The solid angle may be based on the position of the short axial FOV scanner 110 during data capture.

At step 212, the distributed singles (e.g., events) are normalized per organ 220d. The distributed singles are normalized based on the distributed activity generated at step 210 and the average single per block rate 220e. The normalized distributed singles are equal to an average singles per block 234 for a long axial FOV system 120. At step 214, patient specific parameters for a long axial FOV scanner 120 are determined based on the average singles per block 234 determined at step 212, the patient dose and weight 220f used for the short axial FOV scanner 110, and/or a performance model 240 for a long axial FOV scanner 120. The performance model 240 for the long axial FOV scanner 120 may be predetermined based on modeling of the long axial FOV scanner 120. In some embodiments, the patient specific parameters of the long axial FOV scanner 120 include a suggested dose strength 238 for the patient based on the specific long axial FOV scanner 120 and a performance value for requested activity 242. In some embodiments, the suggested dose strength 238 for the long axial FOV scanner 120 is less than the dose used for the short axial FOV scanner 110.

Figure 5:
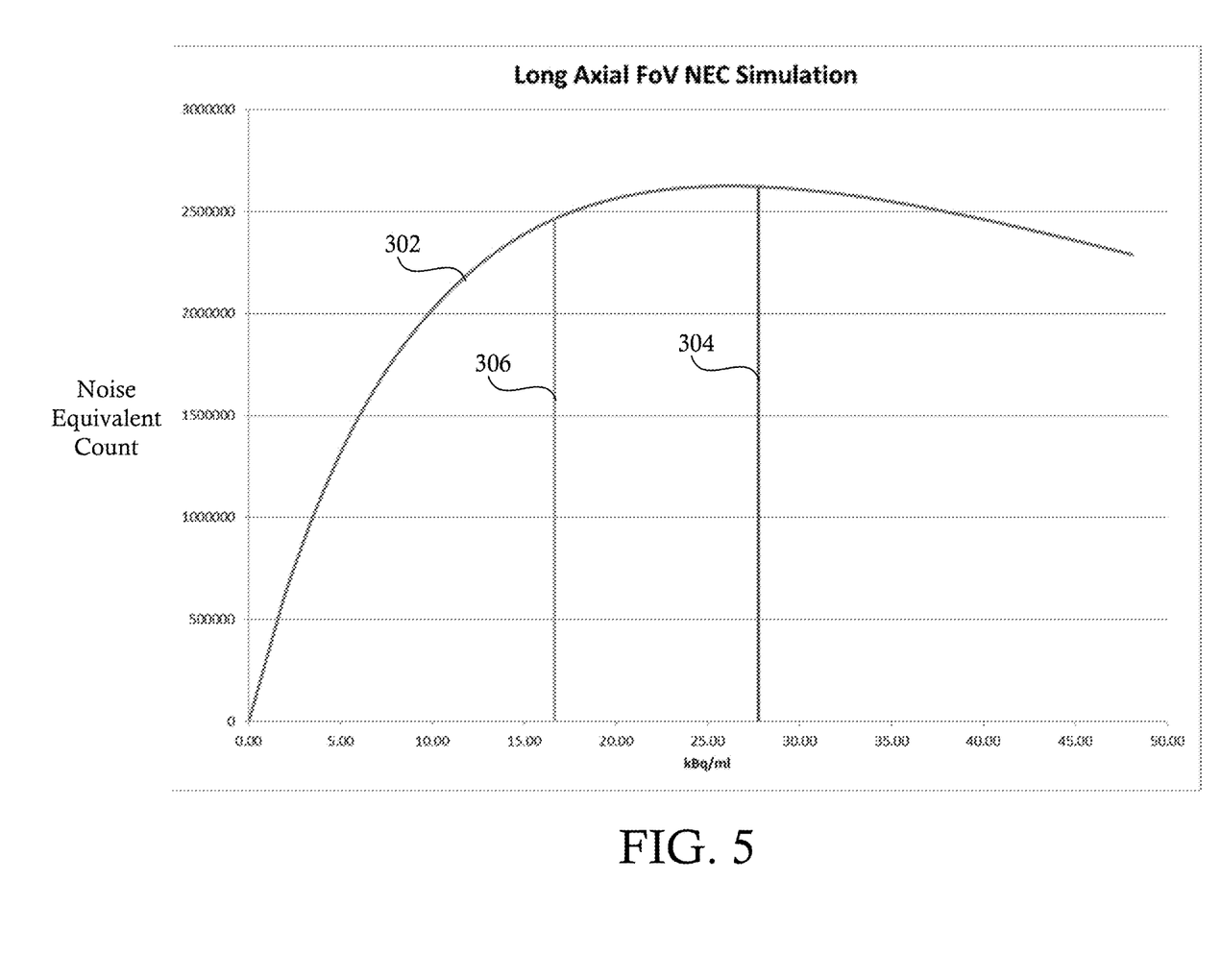
FIG. 5 is a graph illustrating a dosage distribution for a long axial FOV system, in accordance with some embodiments.

FIG. 5 is a graph 300 illustrating a dosage distribution 302 for a long axial FOV system 120, in accordance with some embodiments. The graph 300 includes an x-axis showing dosage in kilobecquerels (kBq) per milliliter (ml) and a y-axis showing a noise equivalent count (NEC). A dosage distribution 302 includes an estimated noise equivalent count (NEC) curve for a predetermined long axial FOV scanner 120. A first position 304 on the dosage distribution 302 corresponds to a recommended dosage that does not account for prior patent imaging data and/or the long axial FOV scanner performance model. A second position 306 corresponds to an optimized dosage for the specific patient and the specific long axial FOV scanner 120. As illustrated in FIG. 5, the optimized dosage 306 is less than the recommended dosage 304, resulting in a lower exposure of radiation to the patient during imaging. The disclosed method 200 allows a clinician to utilize prior scan data, such as prior short axial FOV PET scan data, to estimate a dose for subsequent long axial FOV scanning.

Figure 6:
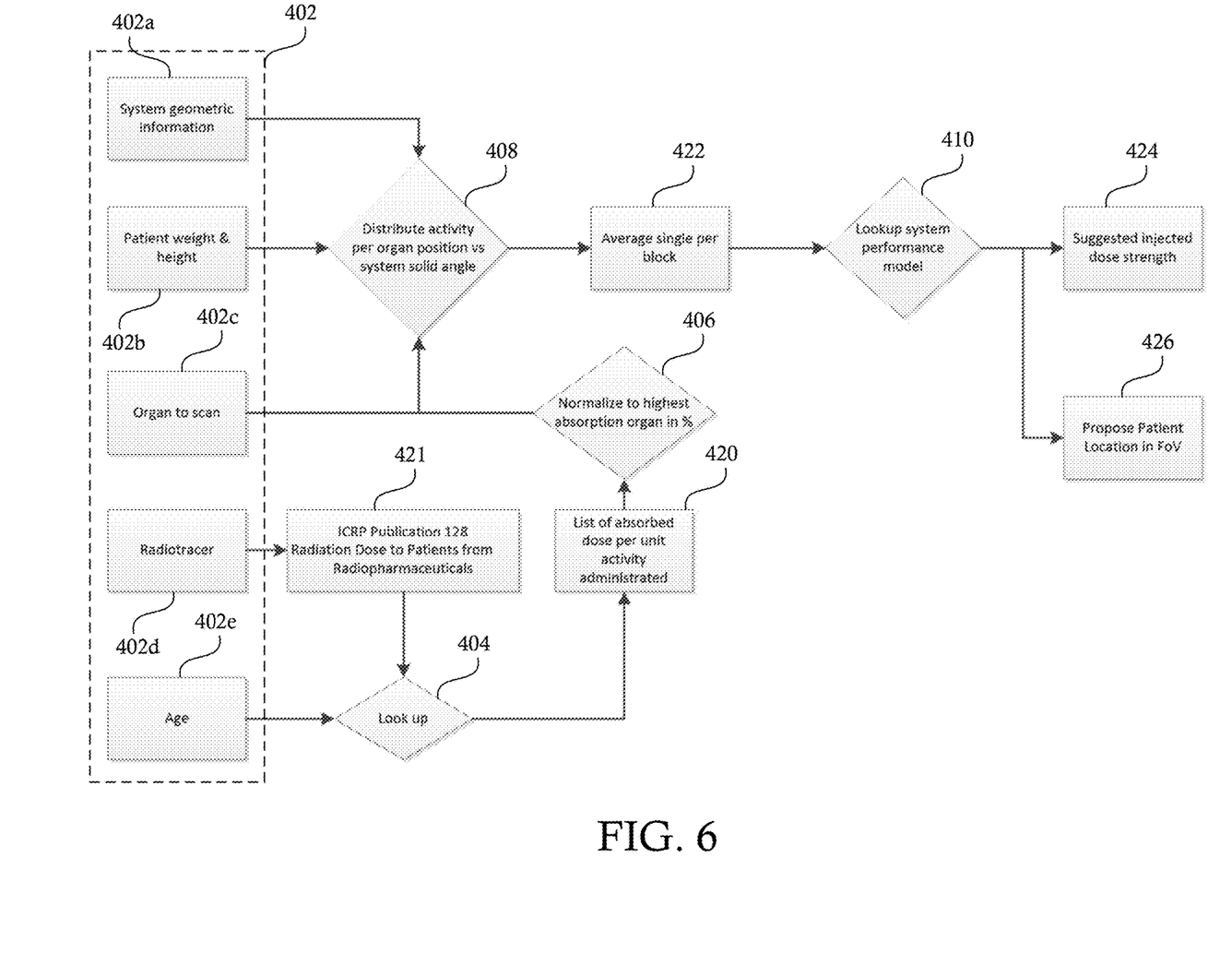
FIG. 6 is a flowchart illustrating a method of generating a patient dosage and position with respect to a large FOV system, in accordance with some embodiments.

FIG. 6 is a flowchart 400 illustrating a method of generating a patient dosage and position with respect to a long axial FOV system, in accordance with some embodiments. A set of prescan data 402 is received by a system, such as the computer system 30. The set of prescan data 402a-402e includes system geometric information 402a for the long axial FOV scanner 120, patient physical statistics 402b such as height and weight, a set of organs to be scanned 402c, a radiotracer identifier 402d, and patient age 402e.

At step 404, an absorbed dose per unit activity 420 is determined based on a patient age 402e and a data set correlating the radiotracer identifier 402d to dosage information, such as, for example, as provided in publicly available data 421 sets such as the ICRP Publication 128 "Radiation Dose to Patients from Radiopharmaceuticals: A Compendium of Current Information Related to Frequently Used Substances" and/or proprietary data sets. The absorbed dose per unity activity 420 may be determined, for example, by use of a look-up table, although it will be appreciated that any suitable method of identifying the absorbed dose per unity activity 420 may be used.

At step 406, the absorbed dose per unity activity 420 and the identification of the set of organs to be scanned 402c is used to normalize the absorbed dose per unity activity 420 to an absorption rate for the organ in the set of organs to be scanned 402c having the highest absorption percentage.

At step 408, the expected event activity (e.g., singles activity) is distributed per organ position for a predetermined (e.g., solid) angle based on the normalized absorbed dose per unity activity 420, the patient physical statistics 402b, and the system geometric information 402a. The distribution of the expected event activity generates an average single (event) per block 422.

At step 410, the system identifies a performance model for the long axial FOV scanner 120 based on the average single per block 422. The performance model includes a suggested injected dose strength 424 and a suggested patient location within the FOV 426. The suggested injected dose strength 424 is patient and long axial FOV scanner 120 specific and the patient location within the FOV 426 is a specific position for the bed within the FOV with respect to the long axial FOV scanner 120. In some embodiments, the computer system 30 is configured to automatically position a patient bed at a suggested patient location within the FOV 426.

In various embodiments, the disclosed methods allow a clinician to identify optimal bed positions and radiotracer dosage levels for producing optimal images. The optimal radiotracer dosage levels are generally lower dosage levels than those suggested for short axial FOV scanners. The disclosed methods adapt the dosage and bed position based on patient body types and age, improve images and reducing dosage, for example, in pediatric imaging. The optimized dosage levels allow a clinician to obtain only a needed dosage for a patient, reducing costs and inventory for radiotracers.

The various computer-implemented methods disclosed herein may be implemented using any suitable methods, systems, or formats. For example, in some embodiments, a computer-implemented method, such as method 200 or method 400 discussed above, may be implemented by a state system, a program, a function, a trained machine learning function, a neural network, etc.

In a first embodiment, a computer-implemented method is disclosed. The method includes receiving a set of prescan parameters, determining an average single per block for a long axial field-of-view (FOV) scanner based on the prescan parameters, and determining at least one scan parameter based on the average single per block for the long axial FOV scanner.

In the computer-implemented method of the first embodiment, the average single per block may be based on a distributed activity per organ position at a predetermined angle of the long axial FOV scanner. The distributed activity per organ may be determined based on an absorption rate normalized to a highest absorption organ rate for a set of target organs.

In any of the preceding embodiments, the set of prescan parameters includes a patient height, a patient weight, and system geometric information for the long axial FOV scanner and the distributed activity per organ is based on a patient body mass index and the system geometric information.

In any of the preceding embodiments, the prescan parameters may include a patient age and a radiotracer identifier and the average single per block may be determined based on an absorbed dose per unit activity administered for the patient age and the radiotracer identifier.

In any of the preceding embodiments, the at least one scan parameter may include a dose strength for an identified radiotracer.

In any of the preceding embodiments, the at least one scan parameter may include a patient bed position within a FOV of the long axial FOV scanner.

In a second embodiment, a system is disclosed. The system includes a long axial FOV scanner and a computer. The computer is configured to receive a set of prescan parameters, determine an average single per block for the long axial field-of-view (FOV) scanner based on the prescan parameters, and determine at least one scan parameter based on the average single per block for the long axial FOV scanner.

In the second embodiment, the average single per block may be based on a distributed activity per organ position at a predetermined angle of the long axial FOV scanner. The distributed activity per organ is determined based on an absorption rate normalized to a highest absorption organ rate for a set of target organs.

In any of the preceding embodiments, the set of prescan parameters may include a patient height, a patient weight, and system geometric information for the long axial FOV scanner and the distributed activity per organ may be based on a patient body mass index and the system geometric information.

In any of the preceding embodiments, the prescan parameters may include a patient age and a radiotracer identifier and the average single per block may be determined based on an absorbed dose per unit activity administered for the patient age and the radiotracer identifier.

In any of the preceding embodiments, the at least one scan parameter may include a dose strength for an identified radiotracer.

In any of the preceding embodiments, the at least one scan parameter may include a patient bed position within a FOV of the long axial FOV scanner.

In a third embodiment, a non-transitory computer-readable medium includes instructions which, when executed by a processor, cause the processor to carry out one or more of the computer implemented methods disclosed herein, such as the computer-implemented method of the first embodiment or any variation thereof.

In a fourth embodiment, a computer-implemented method for determining an optimal dose for a long axial FOV scanner based on data obtained using a short axial FOV scanner is disclosed. The computer-implemented method includes receiving scan data obtained using a short axial FOV scanner and patient data associated with the scan data.

Although the subject matter has been described in terms of exemplary embodiments, it is not limited thereto. Rather, the appended claims should be construed broadly, to include other variants and embodiments, which may be made by those skilled in the art.

What is claimed is:

1. A computer-implemented method, comprising:
   receiving a set of input parameters;
   determining an average single per block for a nuclear imaging scanner having a predetermined field-of-view (FOV) based on the set of input parameters; and
   determining at least one scan parameter based on the average single per block for the nuclear imaging scanner.

2. The computer-implemented method of claim 1, wherein the average single per block is based on a distributed activity per organ positioned within the predetermined FOV nuclear imaging scanner.

3. The computer-implemented method of claim 2, wherein the distributed activity per organ is determined based on an absorption rate normalized to a highest absorption organ rate for a set of target organs.

4. The computer-implemented method of claim 2, wherein the set of input parameters includes patient biometrics and system geometric information for the nuclear imaging scanner, and wherein the distributed activity per organ is based on a patient body mass index and the system geometric information.

5. The computer-implemented method of claim 1, wherein the set of input parameters include patient biometrics and a radiotracer identifier, and wherein the average single per block is determined based on an absorbed dose per unit activity administered for the patient biometrics and the radiotracer identifier.

6. The computer-implemented method of claim 1, wherein the at least one scan parameter includes a dose strength for an identified radiotracer.

7. The computer-implemented method of claim 1, wherein the at least one scan parameter includes a patient position within the predetermined FOV of the nuclear imaging scanner.

8. A system, comprising:
a nuclear imaging scanner; and
a computer configured to:
receive a set of input parameters;
determine an average single per block for a field-of-view (FOV) of the nuclear imaging scanner based on the input parameters; and
determine at least one scan parameter based on the average single per block for the nuclear imaging scanner.

9. The system of claim 8, wherein the average single per block is based on a distributed activity per organ position at a predetermined position within the nuclear imaging scanner.

10. The system of claim 9, wherein the distributed activity per organ is determined based on an absorption rate normalized to a highest absorption organ rate for a set of target organs.

11. The system of claim 9, wherein the set of input parameters includes patient biometrics and system geometric information for the nuclear imaging scanner, and wherein the distributed activity per organ is based on a patient body mass index and the system geometric information.

12. The system of claim 8, wherein the input parameters include patient biometrics and a radiotracer identifier, and wherein the average single per block is determined based on an absorbed dose per unit activity administered for the patient biometrics and the radiotracer identifier.

13. The system of claim 8, wherein the at least one scan parameter includes a dose strength for an identified radiotracer.

14. The system of claim 8, wherein the at least one scan parameter includes a patient bed position within the FOV of the nuclear imaging scanner.

15. A non-transitory computer readable medium storing instructions configured to cause a computer system to execute the steps of:
receiving a set of input parameters;
determining an average single per block for a nuclear imaging scanner having a predetermined field-of-view (FOV) based on the set of input parameters; and
determining at least one scan parameter based on the average single per block for the nuclear imaging scanner.

16. The non-transitory computer readable medium of claim 15 wherein the average single per block is based on the distributed activity corresponding to each organ positioned within the predetermined FOV nuclear imaging scanner.

17. The non-transitory computer readable medium of claim 16, wherein the distributed activity corresponding to each organ is determined based on an absorption rate normalized to a highest absorption organ rate for a set of target organs.

18. The non-transitory computer readable medium of claim 16, wherein the set of input parameters includes patient biometrics and system geometric information for the nuclear imaging scanner, and wherein the distributed activity corresponding to each organ is based on a patient body mass index and the system geometric information.

19. The non-transitory computer readable medium of claim 15, wherein the set of input parameters include patient biometrics and a radiotracer identifier, and wherein the average single per block is determined based on an absorbed dose per unit activity administered for the patient biometrics and the radiotracer identifier.

20. The computer-implemented method of claim 1, comprising:
receiving scan data captured at a scan angle;
determining a location of each scanned organ included within the scan data;
determining a distributed activity of each scanned organ based on each corresponding location and the scan angle; and
generating the set of input parameters based on the distributed activity of each scanned organ.

* * * * *